(12) United States Patent
Yonemaru et al.

(10) Patent No.: US 12,121,042 B2
(45) Date of Patent: Oct. 22, 2024

(54) ADDITIVE COMPOSITION FOR RUMINANT FEEDS

(71) Applicant: AJINOMOTO CO., INC., Tokyo (JP)

(72) Inventors: Sachiko Yonemaru, Kawasaki (JP); Koji Haga, Kawasaki (JP); Yuki Miyazawa, Kawasaki (JP); Susumu Shibahara, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 18/147,860

(22) Filed: Dec. 29, 2022

(65) Prior Publication Data

US 2023/0138420 A1 May 4, 2023

Related U.S. Application Data

(60) Division of application No. 17/034,905, filed on Sep. 28, 2020, now Pat. No. 11,582,988, which is a continuation of application No. PCT/JP2019/013667, filed on Mar. 28, 2019.

(30) Foreign Application Priority Data

Mar. 29, 2018 (JP) ................................ 2018-065682

(51) Int. Cl.
| | |
|---|---|
| A23K 20/142 | (2016.01) |
| A23K 20/158 | (2016.01) |
| A23K 20/174 | (2016.01) |
| A23K 40/25 | (2016.01) |
| A23K 40/35 | (2016.01) |
| A23K 50/10 | (2016.01) |
| A61K 31/198 | (2006.01) |
| A61K 31/405 | (2006.01) |
| A61K 31/455 | (2006.01) |
| A61K 31/519 | (2006.01) |
| A61K 31/714 | (2006.01) |

(52) U.S. Cl.
CPC .......... *A23K 20/142* (2016.05); *A23K 20/158* (2016.05); *A23K 20/174* (2016.05); *A23K 40/35* (2016.05); *A23K 50/10* (2016.05); *A61K 31/198* (2013.01); *A61K 31/405* (2013.01); *A61K 31/455* (2013.01); *A61K 31/519* (2013.01); *A61K 31/714* (2013.01); *A23K 40/25* (2016.05)

(58) Field of Classification Search
CPC .. A23K 20/142; A23K 20/158; A23K 20/174; A23K 40/35; A23K 50/10; A23K 40/25; A61K 31/198; A61K 31/405; A61K 31/455; A61K 31/519; A61K 31/714
USPC ......................................................... 514/52
See application file for complete search history.

(56) References Cited

U.S. PATENT DOCUMENTS

| | | | |
|---|---|---|---|
| 3,804,776 A | 4/1974 | Yazawa et al. | |
| 5,227,166 A | 7/1993 | Ueda et al. | |
| 5,300,297 A | 4/1994 | Ueda et al. | |
| 6,392,075 B1 | 5/2002 | Strohmaier et al. | |
| 8,137,719 B2 | 3/2012 | Bevans et al. | |
| 8,182,851 B2 | 5/2012 | Roman et al. | |
| 9,204,660 B2* | 12/2015 | Nakazawa | ............. A23K 50/10 |
| 9,241,503 B2* | 1/2016 | Nakazawa | ............. A23K 40/35 |
| 9,265,273 B2 | 2/2016 | Nakazawa et al. | |
| 2002/0137958 A1 | 9/2002 | Strohmaier et al. | |
| 2007/0148212 A1 | 6/2007 | Okutani et al. | |
| 2009/0232933 A1 | 9/2009 | Nakazawa et al. | |
| 2011/0081444 A1 | 4/2011 | Nakazawa et al. | |
| 2012/0244248 A1 | 9/2012 | Wright et al. | |
| 2014/0037709 A1 | 2/2014 | Boucher et al. | |
| 2014/0308412 A1 | 10/2014 | Nakazawa et al. | |
| 2019/0166879 A1 | 6/2019 | Shibahara et al. | |

FOREIGN PATENT DOCUMENTS

| | | |
|---|---|---|
| CN | 101980616 A | 2/2011 |
| CN | 105658080 A | 6/2016 |
| EP | 2 274 989 A1 | 1/2011 |
| EP | 2 274 990 A1 | 1/2011 |
| JP | 49-45224 B1 | 12/1974 |
| JP | 5-23114 A | 2/1993 |
| JP | 2005-173 A | 1/2005 |
| JP | 2005-312380 A | 11/2005 |
| JP | 2006-141270 A | 6/2006 |
| JP | 5040919 B2 | 10/2012 |
| WO | WO 2009/122750 A1 | 10/2009 |

(Continued)

OTHER PUBLICATIONS

Search Report issued Jun. 25, 2019 in PCT/JP2019/013667, 12 pages.

(Continued)

*Primary Examiner* — Yih-Horng Shiao
(74) *Attorney, Agent, or Firm* — Oblon, McClelland, Maier & Neustadt, L.L.P.

(57) ABSTRACT

Dispersion type feed additive compositions for ruminants, containing
  (A) at least one selected from hydrogenated vegetable oil and hydrogenated animal oil each having a melting point of higher than 50° C. and lower than 90° C.,
  (B) not less than 0.01 wt % and not more than 6 wt % of a surfactant,
  (C) not less than 16 wt % and not more than 72 wt % of a biologically active substance (excluding L-lysine and a salt thereof), and
  (D) not less than 1 wt % and not more than 40 wt % of L-lysine or a salt thereof,
contain a biologically active substance at a high concentration, show high protection in the rumen, and are also superior in dissolution in the intestinal tract.

5 Claims, 4 Drawing Sheets

(56) References Cited

FOREIGN PATENT DOCUMENTS

| WO | WO 2016/017236 A1 | 2/2016 |
| WO | WO 2017/002594 A1 | 1/2017 |
| WO | WO 2018/030476 A1 | 2/2018 |

OTHER PUBLICATIONS

K. Watanabe et al., "Effects of fat coated rumen bypass lysine and methionine on performance of dairy cows fed a diet deficient in lysine and methionine", Animal Science Journal, 77, 2006, pp. 495-502.

Extended European Search Report issued Dec. 14, 2021 in European Patent Application No. 19775469.0, 9 pages.

C. R. Scholfield, "Composition of Soybean Lecithin" Journal of the American Oil Chemists Society, vol. 58, No. 10, XP055463512, Oct. 1, 1981, pp. 889-892.

Office Action mailed on Nov. 21, 2022, in corresponding Chinese Patent Application No. 201980023241.9, (with English machine translation).

* cited by examiner

ADDITIVE COMPOSITION FOR RUMINANT FEEDS

CROSS REFERENCES TO RELATED APPLICATIONS

This application is a divisional of U.S. application Ser. No. 17/034,905, filed on Sep. 28, 2020, which is a continuation of International Patent Application No. PCT/JP2019/013667, filed on Mar. 28, 2019, and claims priority to Japanese Patent Application No. 2018-065682 filed on Mar. 29, 2018, both of which are incorporated herein by reference in their entireties.

BACKGROUND OF THE INVENTION

Field of the Invention

The present invention relates to feed additive compositions for ruminants. More particularly, the present invention relates to feed additive compositions for ruminants that are provided with high protection in the rumen and are superior in dissolution in the intestinal tract.

Discussion of the Background

When ruminants ingest feed, the microorganisms living in the first stomach (rumen) absorb a part of the nutrients in the feed as a nutrient source. Due to this function, ruminants can absorb, as nutrients, substances that cannot be digested directly. For example, microorganism digests cellulose to produce saccharides and produce volatile organic compounds by fermentation with the saccharides. Ruminants absorb such products as nutrition. On the other hand, a nutrient source desired to be directly absorbed by the ruminant is also digested by the microorganism and the ruminant can absorb only the substances produced by the microorganism by fermentation.

To improve the health condition of ruminants and improve producibility of the products thereof (e.g., cow's milk, edible meat, etc.), it is sometimes desirable to add a nutrient that complements general feeds.

In such cases, to ensure that the biologically active substance (nutrient) is not ingested by microorganisms but effectively absorbed, a feed additive preparation for ruminants that protects the nutrient in the rumen and makes the nutrient absorbed in the intestinal tract after the fourth stomach is used.

In feed preparations for ruminants such as lactating cows and the like, a biologically active substance as a nutrient has conventionally been coated with fat or oil or the like for the purpose of improving protection of the biologically active substance in the rumen. In addition, a fat or oil having a dissolution promoting effect is sometimes used for the purpose of improving dissolution in the intestinal tract and the like. For example, low melting point fats and oils are easily decomposed by intestinal digestive enzymes such as lipase and the like, and it has been reported that dissolution of a biologically active substance in the intestinal tract can be improved by adding such fat or oil (see JP-B-49-45224, which is incorporated herein by reference in its entirety). Also, a substance other than fats and oils is sometimes used. For example, lecithin is sometimes used as a promoter of dissolution of a biologically active substance from a feed preparation in the intestinal tract of ruminants in view of the action thereof as an emulsifier.

On the other hand, when a ruminant ingests a feed preparation, the feed preparation stays in the rumen (the first stomach) for a few hours to some tens of hours, and therefore, a part of the biologically active substance is ingested by the microorganisms always existing in the rumen such as protozoa and the like. Dissolution promoters such as lecithin and low melting point fat or oil induce dissolution of biologically active substances in the rumen and, as a result, a problem occurs that the protection of the feed preparation in the rumen becomes low.

As a method for producing a rumen protected preparation, a dispersion method (matrix type) has been reported which includes melting hydrogenated oil or fat as a protecting agent at a high temperature, substantially uniformly dispersing the main agent therein, and solidifying the mixture as granules by cooling. In the dispersion method, since the main agent is added to the melted protecting agent and the mixture is substantially uniformly mixed, the crystal particles of each single main agent granule are completely covered with the protecting agent. Therefore, even a substance with high water solubility such as lysine hydrochloride can obtain sufficient rumen protection, and granules and pellets having a diameter also have the property of dissolution in the lower intestinal tract.

K. Watanabe et al., Animal Science Journal, 77, p 495-502 (2006), which is incorporated herein by reference in its entirety, reports that both rumen protected methionine preparation and rumen protected lysine preparation have an effect of improving milk yield when administered to dairy cattle; however, it describes that development of a rumen protected preparation by using lysine having higher solubility than methionine is challenging.

JP-B-49-45224, discussed above, describes that when a rumen protected methionine preparation is produced with high melting point oil or fat alone, methionine is easily eluted in water and difficult to be contained in the preparation at not less than 20%. The following JP-A-2005-312380, which is incorporated herein by reference in its entirety, discloses that when lysine hydrochloride is used in place of methionine in the method described in JP-B-49-45224, rumen protection is low and lysine is eluted in the rumen. Thus, it is not easy to apply the same production method to biologically active substances having different properties.

JP-A-2005-312380, which is incorporated herein by reference in its entirety, describes a method for producing a dispersion type rumen bypass agent solidified into a sphere with a diameter of 0.5 to 3 mm by a spray granulation method for spraying a mixture containing hydrogenated oil as a protecting agent, lecithin and a monocarboxylic acid salt of an unsaturated or saturated fatty acid having a carbon number of 12 to 22 into the air at a melting point of the protecting agent (50 to 90° C.). JP-A-2005-312380 discloses that a rumen bypass agent superior in the protection in the first stomach and releaseability in the fourth stomach is obtained by containing lecithin and stearic acid. On the other hand, JP-A-2005-312380 describes that a rumen bypass agent containing 40.0 wt % of a biologically active substance (L-lysine hydrochloride) can be produced by the production method. However, the production method described in JP-A-2005-312380 requires the use of a mixture having a low viscosity for passage through a spray nozzle, and a biologically active substance-containing preparation having a high content exceeding 40 wt % cannot be obtained. Examples of JP-A-2005-312380 disclose a composition containing methionine, lysine, and vitamin $B_1$, and a composition containing methionine, lysine, nicotinic acid, betaine, and taurine. These compositions show a high protection rate of 6 to 16% in the rumen and a high dissolution rate of 81 to 92% in the abomasum. The total amount of biologically active substances contained therein is only about 21%.

JP Patent No. 5,040,919, which is incorporated herein by reference in its entirety, describes a dispersion type feed additive composition for ruminants, which contains at least one kind of a protecting agent selected from a hydrogenated vegetable oil or hydrogenated animal oil having a melting point of higher than 50° C. and lower than 90° C., lecithin, not less than 40 wt % and less than 65 wt % of a basic amino acid and 0.01 to 6 wt % of water. This composition contains a high content of not less than 40 wt % of a basic amino acid. JP-B-5,040,919 describes that the composition has a protection rate improving effect by 0.05 to 6 wt % of lecithin and a protection rate improving effect by controlling water content, and can achieve a high rumen passage rate. Examples of JP-B-5,040,919 disclose a composition containing 40% of lysine hydrochloride and 6% of methionine, and it is disclosed that basic amino acid is contained at a high content of not less than 40 wt %.

US-A-2012/244248, which is incorporated herein by reference in its entirety, describes a ruminant feed additive in which granulated lysine sulfate (particle size 0.3 to 3 mm) is coated with not less than 2 layers (desirably not less than 4 layers) of a mixture of hydrogenated oil and a modifying agent of any of lecithin, stearic acid, oleic acid and palm oil. The content of a biologically active substance (lysine sulfate granulation product) in the feed additive is not less than 50% and less than 60% (not less than 37% and less than 45% based on lysine hydrochloride). The feed additive contains 0.5 to 10% of a modifying agent and, in the Examples of US-A-2012/244248, 2 to 4% of a modifying agent is added. When a modifying agent is used, small scratches, cracks and pinholes in the coating layer of this preparation can be reduced. US-A-2012/244248 describes that the rumen bypass rate of the above-mentioned feed additive is not less than 50% and the small intestine digestion rate is not less than 70%.

On the other hand, the property of a coating type feed additive markedly decreases when a ruminant cracks the feed by chewing.

U.S. Pat. No. 8,137,719, which is incorporated herein by reference in its entirety, describes a preparation produced by uniformly mixing a fatty acid salt, vegetable oil and lysine hydrochloride and molding the obtained pellets. The preparation contains 15 to 25% of a biologically active substance (lysine) and contains 1 to 5% of vegetable oil. In the preparation, vegetable oil is used as a liquefiable conditioner, and not only vegetable oil but also oil, fat, free fatty acid, lipid, lecithin, wax and the like may also be used. U.S. Pat. No. 8,137,719 does not describe a clear role of a liquefiable conditioner, but describes that a fatty acid salt and a liquefiable conditioner form a uniform mixture. The content of the biologically active substance (lysine) described in the Examples of U.S. Pat. No. 8,137,719 is 18.6 to 31% (based on lysine hydrochloride) and the content cannot be said to be high.

U.S. Pat. No. 8,182,851, which is incorporated herein by reference in its entirety, describes a preparation in which lysine hydrochloride is coated with a calcium salt of palm oil distillation residue (PFUD) and fatty acid calcium. In the preparation, the calcium salt is dissolved under acidic conditions after rumen passage and a biologically active substance (lysine hydrochloride) contained in the core is eluted. Examples of U.S. Pat. No. 8,182,851 describe that the concentration of a biologically active substance (lysine hydrochloride) is 20%.

SUMMARY OF THE INVENTION

Accordingly, it is one object of the present invention to provide novel feed additive compositions for ruminants.

It is another object of the present invention to provide novel feed additive compositions for ruminants which contain a biologically active substance at a high concentration, show high protection in the rumen, and are also superior in dissolution in the intestinal tract.

These and other objects, which will become apparent during the following detailed description, have been achieved by the inventors' discovery that dissolution in the intestinal tract can be enhanced while maintaining high protection in the rumen by using a small amount of L-lysine or a salt thereof in combination with a surfactant. Also, the present inventors have found that dissolution in the intestinal tract can be further enhanced while maintaining high protection in the rumen by using a particular amount of a natural vegetable oil in combination with L-lysine or a salt thereof and a surfactant.

Accordingly, the present invention provides the following:

(1) A feed additive composition for ruminants comprising (A) at least one selected from hydrogenated vegetable oil and hydrogenated animal oil each having a melting point of higher than 50° C. and lower than 90° C., (B) not less than 0.01 wt % and not more than 6 wt % of a surfactant, (C) not less than 16 wt % and not more than 72 wt % of a biologically active substance (excluding L-lysine and a salt thereof), and (D) not less than 1 wt % and not more than 40 wt % of L-lysine or a salt thereof.

(2) The composition of (1), wherein the aforementioned L-lysine or a salt thereof is at least one selected from the group consisting of L-lysine, L-lysine hydrochloride, L-lysine sulfate and a salt of L-lysine with carboxylic acid having 1 to 3 carbon atoms.

(3) The composition of (1) or (2), wherein the aforementioned L-lysine or a salt thereof is L-lysine hydrochloride.

(4) The composition of any one of (1) to (3), wherein the aforementioned (D) is not less than 4 wt % and not more than 10 wt % of L-lysine hydrochloride.

(5) The composition of any one of (1) to (4), wherein the aforementioned surfactant is an emulsifier.

(6) The composition of (5), wherein the aforementioned emulsifier is lecithin.

(7) The composition of any one of (1) to (6), further comprising not less than 0.1 wt % and less than 6 wt % of water.

(8) The composition of any one of (1) to (7), further comprising (E) not less than 0.01 wt % and not more than 0.8 wt % of natural vegetable oil.

(9) The composition of (8), wherein the aforementioned (E) is not less than 0.1 wt % and not more than 0.4 wt % of a natural vegetable oil.

(10) The composition of (8) or (9), wherein the aforementioned natural vegetable oil is at least one selected from the group consisting of soybean oil, palm oil, rape seed oil, canola oil, olive oil, almond oil, avocado oil and safflower oil.

(11) The composition of any one of (8) to (10), wherein the aforementioned natural vegetable oil comprises a unsaturated fatty acid having 18 carbon atoms in not less than 60 to 95 wt % relative to the constituent fatty acid of the natural vegetable oil.

(12) The composition of any one of (8) to (11), wherein the aforementioned natural vegetable oil comprises oleic acid in 55 to 90 wt % relative to the constituent fatty acid of the natural vegetable oil.

(13) The composition of any one of (8) to (12), wherein the aforementioned natural vegetable oil is olive oil.

(14) The composition of any one of (1) to (13), wherein the aforementioned biologically active substance is at least one selected from the group consisting of amino acid and vitamin.

(15) The composition of any one of (1) to (13), wherein the aforementioned biologically active substance is at least one selected from the group consisting of arginine, arginine hydrochloride, histidine hydrochloride, valine, leucine, isoleucine, threonine, tryptophan, methionine, sodium glutamate, vitamin $B_{12}$, folic acid and niacin.

(16) The composition of any one of (1) to (15), wherein the aforementioned composition is a dispersion type composition.

(17) The composition of any one of (1) to (15), wherein the aforementioned composition is a coating type composition in which a dispersion type core is coated with a coating agent.

(18) A method for producing a feed additive composition for ruminants, comprising solidifying, in water, a molten mixture of (A) at least one selected from hydrogenated vegetable oil and hydrogenated animal oil each having a melting point of higher than 50° C. and lower than 90° C., (B) a surfactant, (C) a biologically active substance (excluding L-lysine and a salt thereof), and (D) L-lysine or a salt thereof.

(19) The production method of (18), comprising coating the aforementioned molten mixture with a coating agent after solidifying the mixture in water.

(20) The production method of (18) or (19), wherein the aforementioned feed additive composition for ruminants comprises (A) at least one selected from hydrogenated vegetable oil and hydrogenated animal oil each having a melting point of higher than 50° C. and lower than 90° C., (B) not less than 0.01 wt % and not more than 6 wt % of a surfactant, (C) not less than 16 wt % and not more than 72 wt % of a biologically active substance (excluding L-lysine and a salt thereof), and (D) not less than 1 wt % and not more than 40 wt % of L-lysine or a salt thereof.

(21) The production method of any one of (18) to (20), wherein the aforementioned molten mixture further comprises (E) a natural vegetable oil.

(22) The production method of (21), wherein the aforementioned feed additive composition for ruminants comprises (E) not less than 0.01 wt % and not more than 0.8 wt % of a natural vegetable oil.

(23) The production method of any one of (18) to (22), comprising heating the aforementioned molten mixture after solidifying the mixture in water.

(24) A feed additive composition for ruminants comprising (A) at least one selected from hydrogenated vegetable oil and hydrogenated animal oil each having a melting point of higher than 50° C. and lower than 90° C., (B) not less than 1 wt % and not more than 2 wt % of a surfactant, (C) not less than 40 wt % and not more than 72 wt % of histidine hydrochloride, arginine, methionine or valine, and (D) not less than 1.5 wt % and not more than 35 wt % of L-lysine hydrochloride, and not less than 0.1 wt % and less than 6 wt % of water.

(25) The composition of (24), wherein the aforementioned (C) is not less than 40 wt % and not more than 72 wt % of histidine hydrochloride, arginine or valine.

Advantageous Effects of Invention

According to the present invention, a feed additive composition for ruminants that is provided with high protection in the rumen and is superior in dissolution in the intestinal tract can be provided.

The feed additive composition for ruminants of the present invention can further enhance dissolution in the intestinal tract while maintaining high protection in the rumen by using a small amount of L-lysine or a salt thereof in combination with a surfactant as compared to when a surfactant alone is contained.

The feed additive composition for ruminants of the present invention can further enhance dissolution in the intestinal tract while maintaining high protection in the rumen by using a particular amount of a natural vegetable oil in combination with L-lysine or a thereof and a surfactant According to the feed additive composition for ruminants of the present invention, a large amount of a biologically active substance (e.g., amino acid, etc.) can be efficiently transported up to the small intestine of a lactating cow. Therefore, the lactating cow can absorb a large amount of the biologically active substance (e.g., amino acid, etc.) as a nutrient, as a result of which, for example, it is possible to increase milk yield production and the like.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

One of the characteristics of the feed additive composition for ruminants of the present invention (to be also referred to as "the composition of the present invention" in the following) is that it contains (A) at least one selected from hydrogenated vegetable oil and hydrogenated animal oil each having a melting point of higher than 50° C. and lower than 90° C. (to be also referred to as "component A" in the following), (B) surfactant (to be also referred to as "component B" in the following), (C) a biologically active substance (to be also referred to as "component C" in the following), and (D) L-lysine or a salt thereof (to be also referred to as "component D" in the following).

The composition of the present invention preferably further contains water in addition to components A to D.

The composition of the present invention preferably further contains (E) natural vegetable oil (hereinafter sometimes to be referred to as "component E") in addition to components A to D, or components A to D and water.

In the present invention, the term "feed additive composition for ruminants" refers to a composition generally added to a feed for ruminants and ingested when the ruminants ingest the feed. However, it may not necessarily be added to a feed as long as it is ingested by ruminants and, for example, the composition of the present invention may be singly ingested by ruminants.

Component A

In the composition of the present invention, component A acts as a protecting agent. Hydrogenated vegetable oil and hydrogenated animal oil used as component A are obtained by solidifying a vegetable oil or animal oil that is liquid at ordinary temperature (25° C.) by adding hydrogen, and are a concept also including fully hydrogenated oil. The melting point of the hydrogenated vegetable oil and hydrogenated animal oil used in the present invention is generally higher than 50° C., and, since the protection in the rumen may be superior, preferably not less than 55° C., more preferably not less than 60° C. The melting point is generally lower than 90° C., and, since the dissolution in the intestinal tract may be superior, preferably not more than 80° C., more preferably not more than 70° C.

Specific examples of the hydrogenated vegetable oil include soybean hydrogenated oil, palm hydrogenated oil, rape seed hydrogenated oil, canola hydrogenated oil, olive hydrogenated oil, almond hydrogenated oil, avocado hydrogenated oil, peanut hydrogenated oil, cottonseed hydrogenated oil, corn hydrogenated oil, safflower hydrogenated oil, sunflower hydrogenated oil, safflower hydrogenated oil, rice hydrogenated oil, candelilla wax, carnauba wax, rice wax, Japan wax, beeswax and the like, preferably soybean hydrogenated oil or soybean fully hydrogenated oil since they are industrially easily available. Specific examples of the hydrogenated animal oil include beef tallow, lard, whale wax and the like, preferably beef tallow, lard since they are industrially easily available. These hydrogenated vegetable oil and hydrogenated animal oil may be used singly, or two or more kinds thereof may be used in combination.

The content of component A in the composition of the present invention generally exceeds 23 wt %, and, since the protection in the rumen may be superior, is preferably not less than 30 wt %, more preferably not less than 35 wt %, and particularly preferably not less than 40 wt %. The content is generally less than 60 wt %, and, since a high concentration of a biologically active substance can be contained, preferably not more than 55 wt %, more preferably not more than 50 wt %.

Component B

The surfactant used as component B is considered to modify the surface of the biologically active substance and uniformly disperse the active substance in the molten protecting agent without unevenly distributing the substance.

As a specific example, the surfactant may be any of an anion surfactant, a cation surfactant, an amphoteric surfactant, and a nonionic surfactant, and a surfactant having an emulsifying effect is desirable. The composition of the present invention is ingested together with a feed for ruminant animals, and therefore, an emulsifier is one of the preferable surfactants. These surfactants may be used alone, or two or more kinds thereof may be used in combination.

Specific examples of the emulsifier include lecithin, saponin, casein sodium, fatty acid monoglyceride (e.g., stearic acid monoglyceride, oleic acid monoglyceride, etc.), sorbitan fatty acid ester, sucrose fatty acid ester and the like. Among these, lecithin is one of the preferable emulsifiers because it is industrially easily available. These emulsifiers may be used alone, or two or more kinds thereof may be used in combination.

Specific examples of lecithin include plant-derived lecithins such as soybean lecithin, rape lecithin, rapeseed lecithin, sunflower lecithin, safflower lecithin, cottonseed lecithin, corn lecithin, linseed lecithin, sesame lecithin, rice lecithin, coconut lecithin, palm lecithin and the like; egg-yolk lecithin and the like, preferably plant-derived lecithin, more preferably soybean lecithin, since they are industrially easily available. These lecithins may be, for example, hydrogenated product, enzyme treatment product, enzyme decomposition product, lecithin fractionated product or the like. These lecithins may be used singly, or two or more kinds thereof may be used in combination.

The content of component B in the composition of the present invention is generally not less than 0.01 wt % and, since the protection in the rumen could be superior, preferably not less than 0.5 wt %, more preferably not less than 0.5 wt %, further preferably not less than 1 wt %. The content is generally not more than 6 wt % and, since the protection in the rumen could be superior, preferably not more than 5 wt %, more preferably not more than 3 wt %, and particularly preferably not more than 2 wt %.

Component C

The biologically active substance used as component C is not particularly limited as long as it is a substance capable of exhibiting a bioactive function in vivo when ingested by ruminants. For example, amino acid, vitamin, vitamin-like substance, enzyme, protein, peptide and the like can be mentioned. From the aspect of probiotics, it is preferably amino acid or vitamin.

The amino acid may be a free amino acid, or a physiologically acceptable salt. Examples of the physiologically acceptable salt of amino acid include salts with inorganic bases, salts with inorganic acids and salts with organic acids and the like. Examples of the salt with inorganic base include salts with alkali metals such as sodium, potassium, lithium and the like, salts with alkaline earth metals such as calcium, magnesium and the like, ammonium salt and the like. Examples of the salt with inorganic acid include salts with hydrohalic acid (hydrochloric acid, hydrobromic acid, hydroiodic acid, etc.), sulfuric acid, nitric acid, phosphoric acid or the like. Examples of the salt with organic acid include salts with formic acid, acetic acid, propionic acid, oxalic acid, succinic acid, maleic acid, fumaric acid, citric acid or the like. Any of L-form, D-form and DL-form of amino acid can be used, and preferred is L-form or DL-form, and further preferred is L-form.

Specific examples of amino acid include basic amino acid such as arginine, histidine, lysine, hydroxylysine, ornithine, citrulline and the like or a physiologically acceptable salt thereof; neutral amino acid such as glycine, alanine, valine, leucine, isoleucine, serine, threonine, asparagine, glutamine, tryptophan, 5-hydroxytryptophan, cystine, cysteine, methionine, proline, hydroxyproline, phenylalanine, tyrosine and the like or a physiologically acceptable salt thereof; acidic amino acid such as aspartic acid, glutamic acid and the like or a physiologically acceptable salt thereof and the like. From the aspects of protection in the rumen and dissolution in the intestinal tract, arginine, histidine, valine, leucine, isoleucine, threonine, tryptophan, methionine, glutamic acid and physiologically acceptable salts thereof are preferable, arginine, histidine hydrochloride, valine, and methionine are more preferable, and arginine, histidine hydrochloride, and valine are particularly preferable. These amino acids may be used alone, or two or more kinds thereof may be used in combination.

The amino acid and a physiologically acceptable salt thereof may be any of those obtained by extraction and purification from naturally occurring animals, plants and the like, or those obtained by chemical synthesis method, fermentation method, enzymatic method or gene recombination method may be used. Alternatively, a commercially available product may be used as it is or after pulverizing. When amino acid is pulverized, the particle size thereof is preferably not more than 100 μm, more preferably not more than 75 μm.

Specific examples of vitamin include water-soluble vitamins such as vitamin $B_1$, vitamin $B_2$, vitamin $B_6$, vitamin $B_{12}$, folic acid, niacin, pantothenic acid, biotin, vitamin C and the like. From the aspects of protection in the rumen and dissolution in the intestinal tract, it is preferably vitamin $B_{12}$, folic acid, or niacin. These vitamins may be used alone, or two or more kinds thereof may be used in combination, and an appropriate one may be selected.

From the aspects of protection in the rumen and dissolution in the intestinal tract, component C is preferably at least one selected from the group consisting of arginine, arginine hydrochloride, histidine hydrochloride, valine, leucine, isoleucine, threonine, tryptophan, methionine, sodium glutamate, vitamin $B_{12}$, folic acid and niacin, more preferably at least one selected from the group consisting of arginine, histidine hydrochloride and valine.

In the present invention, a particular amount of L-lysine or a salt thereof is used as component D (described later), and component C preferably excludes L-lysine and a salt thereof.

The content of component C in the composition of the present invention is generally not less than 16 wt % and, since a large amount of a biologically active substance can be efficiently afforded, preferably not less than 35 wt %, more preferably not less than 38 wt %, and particularly preferably not less than 38 wt %. The content is generally not more than 72 wt % and, since protection in the rumen could be superior, preferably less than 65 wt %, more preferably not more than 60 wt %, and particularly preferably not more than 50 wt %. When a biologically active substance in a salt form (e.g., salt of amino acid, etc.) is used as component C, the amount thereof is calculated in terms of free form.

Component D

Component D may be free L-lysine, or a salt of L-lysine. Examples of the salt of L-lysine include salts with organic bases, salts with inorganic acids, salts with organic acids, and the like. Examples of the salts with organic bases include salts with alkali metals such as sodium, potassium, lithium and the like, salts with alkaline earth metals such as calcium, magnesium and the like, ammonium salt and the like. Examples of the salt with inorganic acid include salts with hydrohalic acid (hydrochloric acid, hydrobromic acid, hydroiodic acid, etc.), sulfuric acid, nitric acid, phosphoric acid or the like. Examples of the salt with organic acid include salts with carboxylic acid having 1 to 3 carbon atoms (e.g., formic acid, acetic acid, propionic acid), oxalic acid, succinic acid, maleic acid, fumaric acid, citric acid or the like. These salts with L-lysine may be used alone, or two or more kinds thereof may be used in combination.

Component D is preferably at least one selected from the group consisting of L-lysine, a salt of L-lysine with an inorganic acid, and a salt of L-lysine with an organic acid, more preferably at least one selected from the group consisting of L-lysine, L-lysine hydrochloride, L-lysine sulfate, and a salt of L-lysine with carboxylic acid having 1 to 3 carbon atoms, and particularly preferably L-lysine hydrochloride.

L-lysine or a salt thereof used as component D may be any of those extracted and purified from naturally occurring animals and plants, or those obtained by a chemical synthesis method, a fermentation method, an enzyme method or a gene recombination method. Alternatively, a commercially available product may be used as it is or used after pulverization. When component D is pulverized, the particle size thereof is preferably not more than 100 μm, more preferably not more than 75 μm.

The content of component D in the composition of the present invention is generally not less than 1 wt %. From the aspects of protection in the rumen and dissolution in the intestinal tract of component C, it is preferably not less than 1.5 wt %, more preferably not less than 3 wt %, and particularly preferably not less than 4 wt %. The content is generally not more than 40 wt %. From the aspects of protection in the rumen and dissolution in the intestinal tract of component C, it is preferably not more than 35 wt %, more preferably not more than 24 wt %, still more preferably not more than 16 wt %, further preferably not more than 12 wt %, and particularly preferably not more than 8 wt %. When a salt of L-lysine is used as component D, the amount of the salt is calculated in terms of free form (L-lysine).

Component E

The natural vegetable oil used as component E refers to a vegetable oil which is liquid at ordinary temperature (25° C.), and is a concept distinguished from the hydrogenated vegetable oil possibly used for component A.

Specific examples of the natural vegetable oil include soybean oil, palm oil, rape seed oil, canola oil, olive oil, almond oil, avocado oil, safflower oil, sunflower oil, corn oil, rice oil and the like. Preferred are soybean oil, palm oil, rape seed oil, canola oil, olive oil, almond oil, avocado oil and safflower oil. These natural vegetable oils may be used alone, or two or more kinds thereof may be used in combination. These natural vegetable oils may be subjected to a treatment such as transesterification, fractionating treatment and the like as long as it is liquid at ordinary temperature.

While the kind of the fatty acid (constituent fatty acid) constituting component E is not particularly limited, for example, saturated or unsaturated fatty acid having 12 to 24 carbon atoms such as lauric acid, myristic acid, palmitic acid, pulmitoleic acid, stearic acid, oleic acid, linoleic acid, linolenic acid, arachidic acid, behenic acid and the like can be mentioned. From the aspect of dissolution in the intestinal tract, component E preferably includes unsaturated fatty acids having 18 carbon atoms such as oleic acid, linoleic acid, linolenic acid and the like.

While the constitution rate of saturated and unsaturated fatty acids in component E is not particularly limited, component E preferably contains 60 to 95 wt %, more preferably 80 to 95 wt %, of unsaturated fatty acid having 18 carbon atoms, relative to the constituent fatty acid of component E, since in vitro assumed efficacy rate could be superior.

Component E preferably contains 55 to 90 wt %, more preferably 70 to 90 wt %, of oleic acid relative to the constituent fatty acid of component E. Specific examples of component E containing 55 to 90 wt % of oleic acid relative to the constituent fatty acid include olive oil and the like.

While the unsaturation rate of fatty acid having 18 carbon atoms contained in component E (rate of weight of unsaturated fatty acid having 18 carbon atoms to the total weight of saturated fatty acid and unsaturated fatty acid having 18 carbon atoms) is not particularly limited, it is generally not less than 40% and, since in vitro assumed efficacy rate could be superior, preferably not less than 50%, more preferably not less than 55%. While the upper limit of the unsaturation rate is not particularly limited, it is generally 100%.

When the composition of the present invention contains component E, the content of component E in the composition of the present invention is generally not less than 0.01 wt % and, since the in vitro assumed efficacy rate could be superior, preferably not less than 0.05 wt %, more preferably not less than 0.1 wt %. The content is generally not more than 0.8 wt % and, since the in vitro assumed efficacy rate could be superior, preferably not more than 0.6 wt %, more preferably not more than 0.4 wt %.

Water contained in the composition of the present invention is considered to affect the preservation stability of the composition of the present invention and improve protection in the rumen. Water contained in the composition of the present invention is not particularly limited as long as it is generally used for producing feed additive compositions and, for example, ultrapure water, pure water, ion exchange water, distilled water, purified water, tap water and the like can be mentioned.

The content of water (water content) in the composition of the present invention is generally not less than 0.1 wt % and, since the protection in the rumen could be superior, preferably not less than 2 wt %. The content is generally less than 6 wt % and, since the protection in the rumen could be superior, preferably not more than 5 wt %, more preferably not more than 4 wt %.

The water content of the composition of the present invention can be determined by measuring an amount of decrease after heating at 105° C. for 20 min by Kett moisture analyzer (infrared Moisture Balance FD-610).

The composition of the present invention may contain, besides components A to D, optional component E, water, and other component other than those. Such other component is not particularly limited as long as the object of the present invention is not impaired. For example, excipients such as calcium carbonate, silicon dioxide and the like; lubricants such as magnesium stearate, calcium stearate, talc and the like; pH adjusters such as sodium hydrogen carbonate, citric acid and the like; anticaking agents such as calcium silicate, sodium aluminosilicate and the like; and the like can be mentioned. Such other component may be used singly, or two or more kinds thereof may be used in combination.

The composition of the present invention is preferably formed in a shape easily ingestible for ruminants. While the shape is not particularly limited, for example, spherical, granular, pellet shape, rugby ball shape, pressed barley shape, hen's egg shape and the like can be mentioned.

It is preferable that the composition of the present invention has a spherical or a shape similar thereto. While the particle size of a molded product of the composition of the present invention is not particularly limited, it is generally 0.1 to 20 mm and, from the aspect of mixing level with a feed, preferably 0.3 to 10 mm, more preferably 0.5 to 5 mm. The particle size of the composition of the present invention is defined by sieve analysis using the standard sieve defined in JIS Z 8801 of Japanese Industrial Standards, which is incorporated herein by reference in its entirety.

The production method of the composition of the present invention is not particularly limited, and the composition of the present invention may be produced by a method known per se. For example, it can be produced by the method described in WO2008/041371, US-A-2009/0232933, WO2009/122750, US-A-2011/0081444, all of which are incorporated herein by reference in their entireties, or a method analogous thereto. Specifically, the composition of the present invention can be produced by a method including solidifying a molten mixture containing components A to D or components A to E in water or the like.

Each content of components A to D in the molten mixture can be appropriately set according to each content of components A to D in the composition of the present invention to be produced. The content of component A in the molten mixture is generally more than 23 wt % and less than 60 wt %, preferably not less than 30 wt % and not more than 55 wt %, more preferably not less than 30 wt % and not more than 50 wt %, and particularly preferably not less than 35 wt % and not more than 50 wt %; the content of component B in the molten mixture is generally not less than 0.01 wt % and not more than 6 wt %, preferably not less than 0.05 wt % and not more than 6 wt %, more preferably not less than 0.5 wt % and not more than 3 wt %, and particularly preferably not less than 1 wt % and not more than 2 wt %; the content of component C in the molten mixture is generally not less than 16 wt % and not more than 72 wt %, preferably not less than 35 wt % and not more than 72 wt %, more preferably not less than 40 wt % and not more than 72 wt %, further preferably not less than 40 wt % and less than 65 wt %, and particularly preferably not less than 40 wt % and not more than 60 wt %; and the content of component D in the molten mixture is generally not less than 1 wt % and not more than 40 wt %, preferably not less than 1.5 wt % and not more than 35 wt %, more preferably not less than 2 wt % and not more than 30 wt %, still more preferably not less than 2 wt % and not more than 20 wt %, further preferably not less than 4 wt % and not more than 20 wt %, and particularly preferably not less than 5 wt % and not more than 10 wt %.

When the molten mixture contains component E, the content thereof can be appropriately set according to the content of component E in the composition of the present invention to be produced. The content of component E in the molten mixture is generally not less than 0.01 wt % and not more than 0.8 wt %, preferably not less than 0.05 wt % and not more than 0.6 wt %, and more preferably not less than 0.1 wt % and not more than 0.4 wt %.

A preparation method of the molten mixture containing components A to D or components A to E is not particularly limited and, for example, a method including heating components A to D or components A to E (optionally containing other component when desired) using a commercially available extruder (preferably, twin screw extruder) and the like, and the like can be mentioned. The order of addition of components A to D or components A to E to a cylinder of the extruder is not particularly limited. To coat the surface of component C with component B, the components B and C may be mixed with a Nauta mixer or the like before addition, or components A to D or components A to E may be added almost simultaneously to increase production efficiency. Alternatively, the molten mixture can also be obtained by mixing components A and C in advance at around room temperature, adding the remaining components and heating the mixture. Component C may be pulverized before use. For example, component C may be used after pulverizing with a pulverizer to a particle size of preferably not more than 100 μm, more preferably not more than 75 μm, and sieving as necessary.

The temperature at which components A to D or components A to E are heated is not particularly limited as long as it is not less than the melting point of component A. It is preferably 5 to 15° C. higher than the melting point of component A. For example, when soybean fully hydrogenated oil (melting point: 67 to 71° C.) is used as component A, it is heated at 80 to 85° C. In this case, the component other than component A is not necessarily melted. For example, when L-histidine hydrochloride (melting point: about 254° C.) is used as component C, L-histidine hydrochloride may be dispersed without melting and the molten mixture may be in a slurry state. It is not necessary to heat at a temperature not less than the melting point of component A from the beginning of heating. A stable molten mixture is obtained efficiently by, for example, first preheating materials at a temperature 5 to 10° C. lower than the melting point of component A, then conveying the materials by a screw in the cylinder of the extruder, and then heating them at a predetermined temperature not less than the melting point of component A.

The instrument that can be utilized for preparing the molten mixture is not limited to the extruder, and any instrument may be used appropriately as long as it can prepare a molten mixture that can become a droplet when dropped naturally.

The method for solidifying the molten mixture containing components A to D or components A to E in water is not particularly limited. For example, a method including retaining the molten mixture in a container having a hole (pore) with a predetermined diameter and dropping the molten mixture into water from the hole, and the like can be mentioned. When the molten mixture is dropped (preferably, free fall) from the hole with a predetermined diameter, it is cleaved by the action of surface tension during dropping to become respectively independent droplets. When the droplet is dropped into a water tank at a given temperature, the droplet is instantaneously cooled in water to solidify and a solid with a given shape is obtained. When the droplet solidifies into solid, the water in the water tank is taken into the solid. This water taken into the solid can be decreased by subjecting the solid to a heating treatment (described later). When the molten mixture is solidified in water, a part of the biologically active substance may be dissolved in water; however, the amount thereof is extremely small.

The diameter of the hole in the container retaining the molten mixture may be appropriately selected according to the size of the finally-obtained solid (solidified droplet of the molten mixture). For example, when a solid with a particle size of about 3 to 5 mm is produced, the diameter of the hole only needs to be set to 0.5 to 3 mm, and when a solid with a particle size of about 5 to 10 mm is produced, the diameter of the hole only needs to be set to 3 to 5 mm. The diameter of the hole in the container for storing a molten mixture is generally 0.5 to 5 mm, preferably 1 to 4 mm.

While the container retaining the molten mixture is not particularly limited as long as it has a hole with a predetermined diameter, a multi-hole shooter is preferably used since it can efficiently increase the production amount. Here, the "multi-hole shooter" refers to a container having a plurality of perforations in the bottom and a facility for temporarily retaining the molten mixture. The container for retaining the molten mixture is preferably provided with a heat facility to prevent cooling of the molten mixture to be retained.

The drop distance (e.g., distance from the bottom surface of the multi-hole shooter to water surface) of the molten mixture is not particularly limited and it is generally 10 mm to 1.5 m, preferably 30 mm to 1.0 m. The shape of the finally-obtained solid can be changed by adjusting the drop distance of the molten mixture. For example, when a molten mixture heated to about 65° C. is dropped into water, a drop distance of 50 to 150 mm affords a solid with a spherical shape to a rugby ball-like shape. A longer drop distance leads to a large impact energy with the water surface, and a solid with a shape of flattened pressed barley is obtained. For example, when the drop distance is about 0.5 m, a solid with a shape of pressed barley with an undulating fringe is obtained.

The temperature of the molten mixture when dropped into water is not particularly limited and is generally 60 to 90° C., and preferably 70 to 90° C. in view of the melting point of component A and the like.

The temperature of water into which the molten mixture is dropped is not particularly limited as long as the molten mixture is instantaneously solidified, and is generally 0 to 30° C.

A method for collecting a mixture solidified in water is not particularly limited. When the water temperature is to be maintained constant by continuously supplementing water, the solidified mixture (specific gravity: about 1.1) may be collected using a net, a net container or the like.

When the composition of the present invention is produced by a method including solidifying a molten mixture containing components A to D or components A to E in water, the method preferably further includes heating the solidified mixture. By heating the solidified mixture, the mixture can be dried and the water content of the composition of the present invention can be controlled. The solidified mixture can be heated, for example, by exposing the solidified mixture generally for several minutes to several tens of minutes to an atmosphere (e.g., hot water, vapor, hot air, etc.) set to a temperature lower than the melting point of component A contained in the solidified mixture, or the like. The time of the heating can be appropriately determined based on the temperature of the heating, the kind of component A, the amount of the solidified mixture and the like. For example, the solidified mixture may be exposed for a long time (e.g., 0.5 to 2 hr, etc.) to an atmosphere set to a temperature lower than the melting point of component A contained in the solidified mixture.

When the composition of the present invention is produced by a method including solidifying a molten mixture containing components A to D or components A to E in water, the method preferably may further include coating the solidified mixture with a coating agent. Examples of the usable coating agent include hydrogenated oil, surfactant, natural vegetable oil, animal oil, vegetable oil, fatty acid or a salt thereof, wax, wax, polysaccharides (chitosan, alginic acid, etc.), monoglyceride, diglyceride, triglyceride, fatty acid ester, fatty acid alcohol, celluloses (carboxymethyl cellulose, etc.), clay, silica, pH sensitivity polyvinyl derivative (polyvinylpyrrolidone, etc.), acrylic resin (resin No. IV, etc.) and the like. The method for coating the solidified mixture is not particularly limited and a method known per se can be adopted for coating. For example, the methods described in U.S. Pat. Nos. 8,137,719, 8,182,851, which are incorporated herein by reference in their entireties, and the like or a method analogous thereto can be used for the production.

In one embodiment, the composition of the present invention may be a dispersion type composition. As used herein, the "dispersion type" feed additive composition for ruminants refers to a feed additive composition for ruminants containing each component containing a biologically active substance in a state where the component is dispersed substantially uniformly. In another embodiment, the composition of the present invention may be a coating type composition in which a dispersion type core is coated with a coating agent. As used herein, a feed additive composition for ruminants of the "coating type in which a dispersion type core is coated with a coating agent" refers to a feed additive composition for ruminants in which the center part (core) is a dispersion type (containing each component containing a biologically active substance in a state where the component is substantially uniformly dispersed) and the surface of the core is coated with a coating agent.

The composition of the present invention preferably has a layer substantially free of a biologically active substance as the surface layer thereof. The composition of the present invention may have water-repellency by the presence of a layer substantially free of a biologically active substance as the surface layer. As used herein, the "layer substantially free of a biologically active substance" means either a layer completely free of a biologically active substance or a layer containing a biologically active substance in an amount not inhibiting water-repellency (generally not more than 2 wt %, preferably not more than 1 wt %).

The thickness of the layer substantially free of a biologically active substance is generally 30 to 110 μm and, since water-repellency could be superior, preferably 30 to 80 μm.

The composition of the present invention having a layer substantially free of a biologically active substance as the surface layer can be produced by, for example, the aforementioned production method, that is, a method including solidifying a molten mixture containing components A to D or components A to E in water and subjecting the solidified mixture to heating or the like. The layer substantially free of a biologically active substance is considered to be formed because the biologically active substance on the surface is dissolved in water when the molten mixture is solidified in water and then the surface of the solidified mixture is smoothened by the heat treatment. The composition of the present invention having a layer substantially free of a biologically active substance as the surface layer can also be produced by, for example, a method including solidifying a molten mixture containing components A to D or components A to E in water, and coating the solidified mixture with a coating agent, or the like.

The protection in the rumen and dissolution in the intestinal tract of the composition of the present invention can be evaluated by the following method.

In the following method, the concentration of the biologically active substance in the test solution is measured by liquid chromatography (manufactured by HITACHI).

Measurement of Concentration (Concentration A) of Biologically Active Substance for Calculation of Protection Rate Using a dissolution tester (manufactured by TOYAMA SANGYO CO., LTD.), a preparation sample (about 3 g) is placed in ultrapure water (900 ml) (produced using Milli Q (manufactured by Millipore)) heated to a temperature (e.g., 39° C.) corresponding to the body temperature of ruminants (e.g., dairy cattle, etc.), and the mixture is stirred at 100 rpm. At 20 hr from the start of stirring, 2 ml of the stirring test solution is collected for protection rate measurement, and the concentration of the biologically active substance is measured (concentration A, unit: mg/dl).

Measurement of Concentration (Concentration B) of Biologically Active Substance for Calculation of Dissolution Rate To the test solution immediately after collection of the above-mentioned sample for protection rate measurement is added with stirring at 100 rpm an aqueous solution (8 ml) of a bile powder (manufactured by Wako Pure Chemical Industries, Ltd.) and pancreatin (manufactured by Wako Pure Chemical Industries, Ltd.) (concentration of bile powder and pancreatin is 23.4 g/100 ml for each) to give a small intestine-corresponding test solution. At 5 hr from the addition of the aqueous solution, 2 ml of the stirring test solution is collected for dissolution rate measurement, and the concentration of the biologically active substance is measured (concentration B, unit: mg/dl).

Calculation of Protection Rate and Dissolution Rate of Biologically Active Substance The protection rate and dissolution rate of biologically active substance are calculated by the following formulas.

$$\text{protection rate [\%]} = \{1-(\text{concentration } A[\text{mg/dl}] \times 9.08)/(\text{preparation sample weight [g]} \times 1000 \times \text{content of biologically active substance in preparation sample [wt \%]}/100)\} \times 100$$

$$\text{dissolution rate [\%]} = \{((\text{concentration } B[\text{mg/dl}] - \text{concentration } A[\text{mg/dl}]) \times 9.02)/(\text{preparation sample weight [g]} \times 1000 \times \text{content of biologically active substance in preparation sample [wt \%]}/100)\} \times 100$$

The in vitro assumed efficacy rate of the composition of the present invention can be calculated from the following formula.

$$\text{in vitro assumed efficacy rate [\%]} = (\text{dissolution rate [\%]}) \times (\text{content [wt \%] of biologically active substance})/100$$

The ruminants for which the composition of the present invention is used are not particularly limited. For example, bovine, sheep, goat, deer, giraffe, camel and llama and the like can be mentioned. Preferred is bovine.

The amount of the composition of the present invention to be added to a feed for ruminants is not particularly limited, and can be appropriately adjusted according to the necessary amount of the biologically active substance and the like. The composition of the present invention is generally added to a feed and used together with the feed to be ingested by the ruminants. However, as long as the composition is ingested by the ruminants, it may not necessarily be added to a feed. For example, the composition of the present invention can be ingested by the ruminants by itself.

Other features of the invention will become apparent in the course of the following descriptions of exemplary embodiments which are given for illustration of the invention and are not intended to be limiting thereof.

EXAMPLES

Experimental Example 1, Histidine Hydrochloride Monohydrate

Example 1

Soybean fully hydrogenated oil (manufactured by Yokozeki Oil & Fat Industries Co., Ltd.), soybean lecithin (manufactured by ADM, Yelkin TS), L-histidine hydrochloride monohydrate (manufactured by Ajinomoto Co., Inc.), L-lysine hydrochloride (manufactured by Ajinomoto Co., Inc.) and olive oil (manufactured by JOM, extra virgin) in the proportions shown in the following Table 1 were continuously cast into a twin screw extruder (manufactured by Cosmotec Co., Ltd.).

Thereafter, the mixture was heated (preheating temperature: 65° C., main heating temperature: 85° C., set temperature for outlet: 70° C.), melted and mixed in a cylinder to give a molten mixture in a molten slurry state. The obtained molten mixture was discharged from the outlet of the extruder, cast into a multi-hole shooter (number of holes: 2060, hole diameter: 2 mm), and the molten mixture was freely dropped from the hole of a multi-hole shooter into the water tank for cooling. The distance from the multi-hole shooter to the water surface of the water tank for cooling was 10 cm. The molten mixture that dropped from the multi-hole shooter became droplet during dropping, solidified in water, cooled and solidified instantaneously. The attached water was dehydrated by blowing at room temperature, and the solid was subjected to a heat-drying treatment by a fluidized-bed dryer (manufactured by Ajinomoto Co., Inc.) set to 52° C. for 7 min to give granules (feed additive composition for ruminants). In the following, the granulated product is referred to as the composition of Example 1.

Examples 2-8, Control H

In the same manner as in Example 1 except that soybean fully hydrogenated oil (manufactured by Yokozeki Oil & Fat Industries Co., Ltd., melting point: 67° C.), soybean lecithin (manufactured by ADM, Yelkin TS), L-histidine hydrochloride monohydrate (manufactured by Ajinomoto Co., Inc.), L-lysine hydrochloride (manufactured by Ajinomoto Co., Inc.) and olive oil (manufactured by JOM, extra virgin) were cast in the proportions shown in the following Table 1, feed additive compositions for ruminants of Examples 2 to 8, and control H (hereinafter to be referred to as composition of Examples 2 to 8, and control) were obtained.

The L-histidine content, L-lysine content, water content, protection rate and dissolution rate shown in Examples 1 to 8, and control H were measured and calculated in the following manner.

Measurement of Content of L-Histidine and Content of L-Lysine in Feed Additive Composition The L-histidine content and L-lysine content of each composition were measured and calculated by the following procedure.

In a 50 ml conical tube manufactured by FALCON, 4.00 g of a feed additive composition (dry matter) after measuring the "content of water in feed additive composition" (described below) and 20.0 g of pure water were weighed and tightly sealed, and the tube was immersed in a constant temperature water bath at 85° C. for 20 min. Soybean hydrogenated oil was melted, hydrogenated oil, L-histidine, and L-lysine were separated to dissolve L-histidine and L-lysine in an aqueous solution. The thus-recovered L-histidine and L-lysine were analyzed by general liquid chromatography (manufactured by HITACHI) and the contents (wt %) of L-histidine and L-lysine in the feed additive composition (dry matter) were respectively determined.

Measurement of Content of Water in Feed Additive Composition

The water content of each composition was determined by measuring, by Kett moisture analyzer (infrared Moisture Balance FD-610), an amount of decrease after heating at 105° C. for 20 min.

Measurement of Protection Rate and Dissolution Rate

The concentration of the biologically active substance (L-histidine) in the following test solutions was measured using liquid chromatography (manufactured by HITACHI).

Measurement of Concentration (Concentration A) of Biologically Active Substance (L-Histidine) for Calculation of Protection Rate Using a dissolution tester (manufactured by TOYAMA SANGYO CO., LTD.), a preparation sample (about 3 g) was placed in ultrapure water (produced using Milli Q (manufactured by Millipore)) (900 ml) heated to 39° C. corresponding to the body temperature of dairy cattle, and the mixture was stirred at 100 rpm. At 20 hr from the start of stirring, 2 ml of the stirring test solution was collected for protection rate measurement, and the concentration of the biologically active substance (L-histidine) was measured (concentration A, unit: mg/dl).

Measurement of Concentration (Concentration B) of Biologically Active Substance (L-Histidine) for Calculation of Dissolution Rate To the test solution immediately after collection of the above-mentioned sample for protection rate measurement was added with stirring at 100 rpm an aqueous solution (8 ml) of a bile powder (manufactured by Wako Pure Chemical Industries, Ltd.) and pancreatin (manufactured by Wako Pure Chemical Industries, Ltd.) (concentration of bile powder and pancreatin is 23.4 g/100 ml for each) to give a small intestine-corresponding test solution. At 5 hr from the addition of the aqueous solution, 2 ml of the stirring test solution was collected for dissolution rate measurement, and the concentration of the biologically active substance (L-lysine) was measured (concentration B, unit: mg/dl).

<Calculation of Protection Rate and Dissolution Rate of Biologically Active Substance (L-Histidine)>

The protection rate and dissolution rate of biologically active substance (L-histidine) were calculated by the following formulas.

$$\text{protection rate (\%)} = \{1-(\text{concentration } A[\text{mg/dl}] \times 9.08)/(\text{preparation sample weight } [g] \times 1000 \times \text{content of biologically active substance in preparation sample } [\text{wt \%}]/100)\} \times 100$$

$$\text{dissolution rate (\%)} = \{((\text{concentration } B[\text{mg/dl}] - \text{concentration } A [\text{mg/dl}]) \times 9.02)/(\text{preparation sample weight } [g] \times 1000 \times \text{content of biologically active substance in preparation sample } [\text{wt \%}]/100)\} \times 100$$

The in vitro assumed efficacy rate of the compositions of Examples 1 to 8, and control H was calculated from the following formula.

$$\text{in vitro assumed efficacy rate } [\%] = (\text{dissolution rate } [\%]) \times (\text{content of biologically active substance } [\text{wt \%}])/100$$

Figure 1:
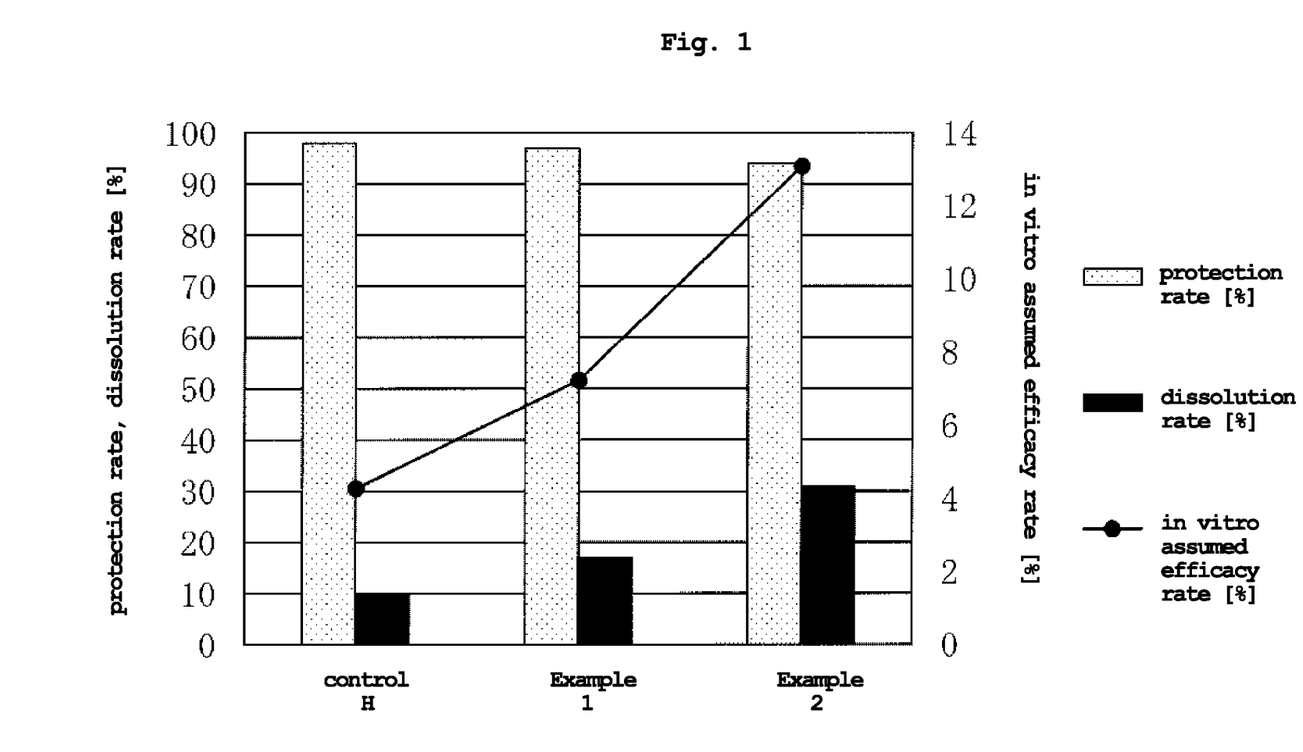
FIG. 1 is a graph showing the protection rate, dissolution rate and in vitro assumed efficacy rate of the compositions of Examples 1 and 2 and control H (no blending of olive oil).
Figure 2:
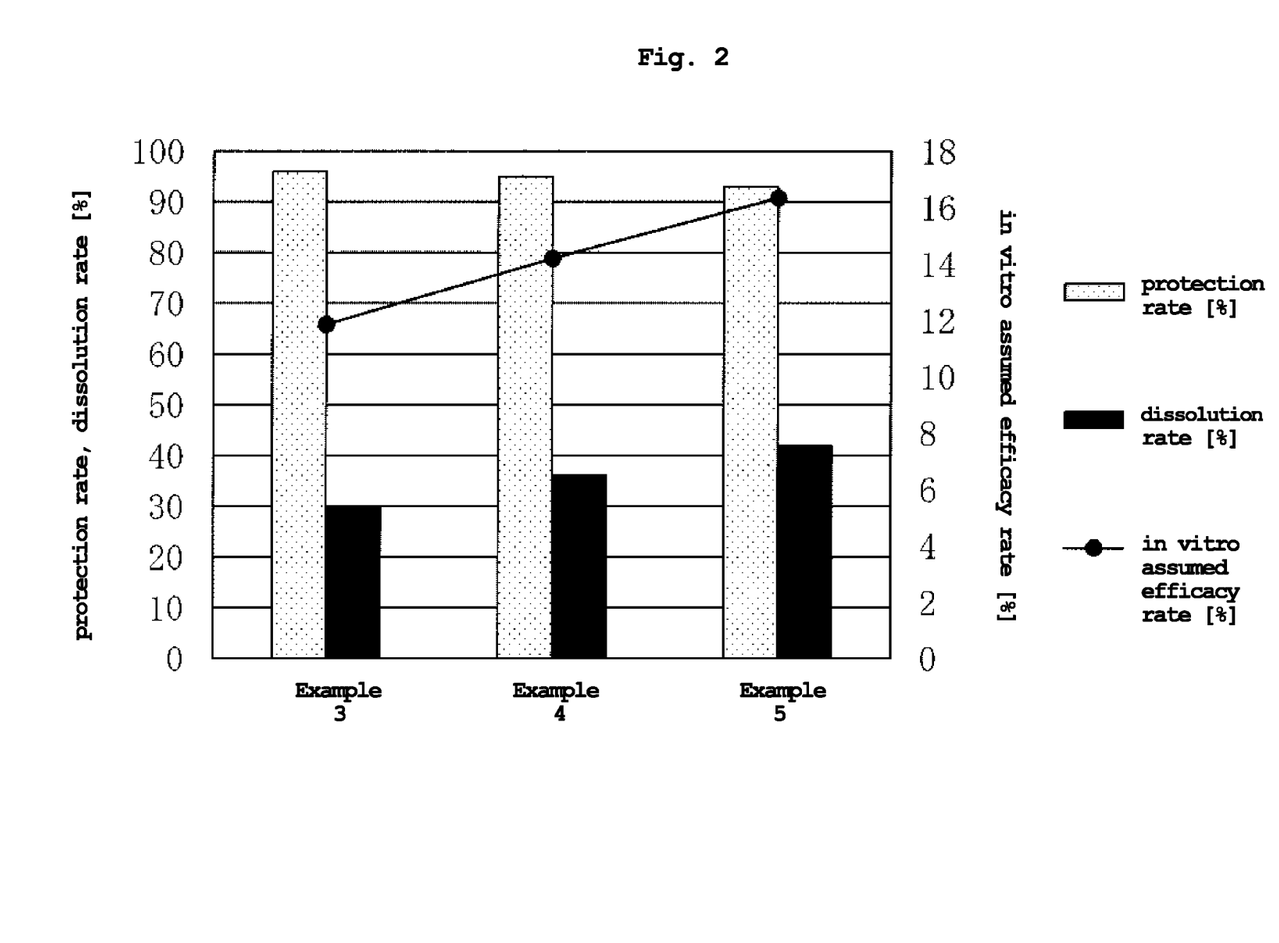
FIG. 2 is a graph showing the protection rate, dissolution rate and in vitro assumed efficacy rate of the compositions of Examples 3 to 5 (blending ratio of olive oil: 0.2 wt %).
Figure 3:
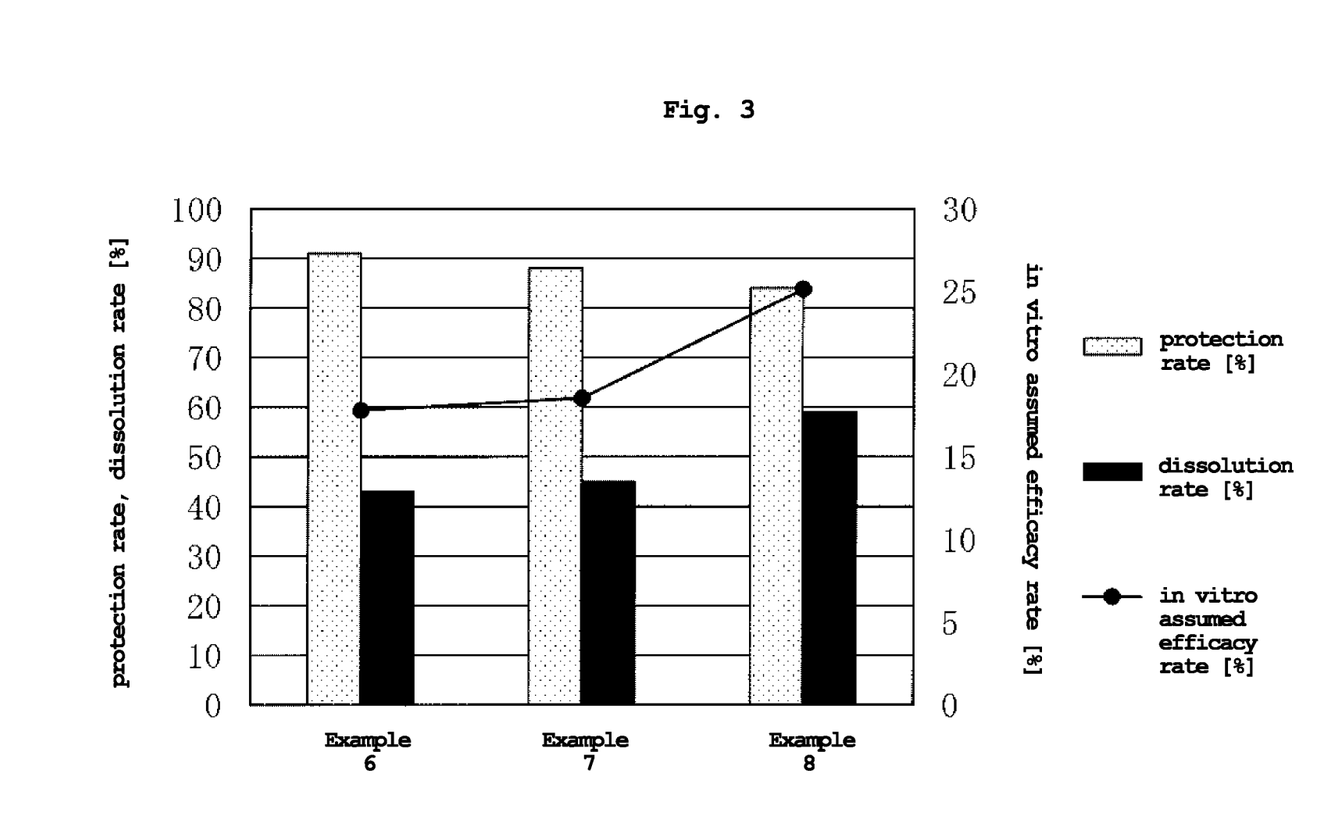
FIG. 3 is a graph showing the protection rate, dissolution rate and in vitro assumed efficacy rate of the compositions of Examples 6 to 8 (blending ratio of olive oil: 0.1 wt %).
Figure 4:
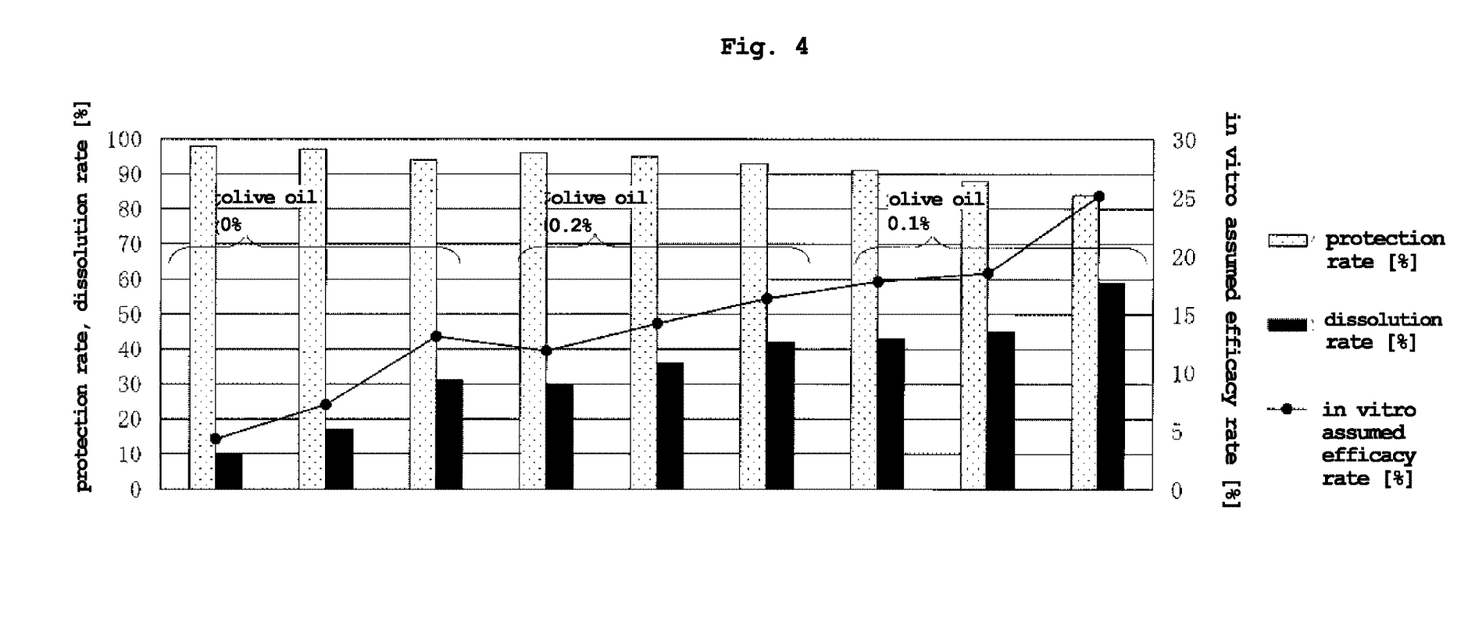
FIG. 4 is a graph showing the protection rate, dissolution rate and in vitro assumed efficacy rate of the compositions of Examples 1 to 8 and control H.

The L-histidine content, water content, protection rate, dissolution rate and in vitro assumed efficacy rate of the compositions of Examples 1 to 8, and control H are shown in the following Table 1 and FIGS. 1 to 4.

The contents of soybean fully hydrogenated oil, soybean lecithin and olive oil in the molten mixture do not change before and after granulation in water.

TABLE 1

| | blending ratio [wt %] | | | | | content of L-histidine in feed additive composition [wt %] | content of L-lysine in feed additive composition [wt %] | content of water in feed additive composition [wt %] | protection rate [%] | dissolution ratio [%] | in vitro assumed efficacy rate [%] |
|---|---|---|---|---|---|---|---|---|---|---|---|
| | (A) soybean fully hydrogenated oil | (B) soybean lecithin | (C) L-histidine hydrochloride | (D) L-lysine hydrochloride | (E) olive oil | | | | | | |
| control H | 38.7 | 1.3 | 60.0 | 0 | 0 | 42.7 | 0.0 | 0.38 | 98 | 10 | 4.3 |
| Example 1 | 36.7 | 1.3 | 60.0 | 2.0 | 0 | 42.5 | 1.6 | 0.47 | 97 | 17 | 7.2 |
| Example 2 | 33.7 | 1.3 | 60.0 | 5.0 | 0 | 42.2 | 3.5 | 0.88 | 94 | 31 | 13.1 |
| Example 3 | 38.5 | 1.3 | 55.0 | 5.0 | 0.2 | 39.5 | 3.7 | 0.31 | 96 | 30 | 11.9 |
| Example 4 | 36.5 | 1.3 | 55.0 | 7.0 | 0.2 | 39.4 | 5.2 | 0.38 | 95 | 36 | 14.2 |
| Example 5 | 34.5 | 1.3 | 55.0 | 9.0 | 0.2 | 38.9 | 6.5 | 0.45 | 93 | 42 | 16.3 |
| Example 6 | 34.5 | 1.4 | 58.0 | 6.0 | 0.1 | 41.4 | 4.3 | 0.55 | 91 | 43 | 17.8 |
| Example 7 | 33.5 | 1.4 | 58.0 | 7.0 | 0.1 | 41.2 | 4.9 | 0.33 | 88 | 45 | 18.5 |
| Example 8 | 32.5 | 1.4 | 58.0 | 8.0 | 0.1 | 42.6 | 5.7 | 0.54 | 84 | 59 | 25.1 |

As is clear from the results shown in Table 1 and FIGS. 1 to 4, the compositions of Examples 1 and 2 showed an improved dissolution rate while maintaining a high protection rate by using a small amount of L-lysine or a salt thereof (L-lysine hydrochloride) and a surfactant (lecithin) in combination as compared to the composition of control H containing a surfactant (lecithin) alone. From the results, it was confirmed that the dissolution in the intestinal tract can be further enhanced while maintaining high protection in the rumen by using a small amount of L-lysine or a salt thereof and a surfactant in combination as compared to when a surfactant alone is contained.

The compositions of Examples 3 to 8 showed a still more improved dissolution rate while maintaining a high protection rate by using a particular amount of a natural vegetable oil in combination with L-lysine or a salt thereof (L-lysine hydrochloride) and a surfactant (lecithin). From the results, it was confirmed that the dissolution in the intestinal tract can be further more enhanced while maintaining high protection in the rumen by using a particular amount of a natural vegetable oil in combination with L-lysine or a salt thereof and a surfactant.

Experimental Example 2, Arginine

Example 9, Control A

In the same manner as in Example 1 except that soybean fully hydrogenated oil (manufactured by Yokozeki Oil & Fat Industries Co., Ltd.), soybean lecithin (manufactured by ADM, Yelkin TS), L-arginine (manufactured by Ajinomoto Co., Inc.), and L-lysine hydrochloride (manufactured by Ajinomoto Co., Inc.) were cast in the proportions shown in the following Table 2, the feed additive compositions for ruminants of Example 9 and control A (hereinafter to be referred to as composition of Example 9 and control A) were obtained.

The L-arginine content, L-lysine content, water content, protection rate, dissolution rate and in vitro assumed efficacy rate of the compositions of Example 9 and control A were measured and calculated in the same manner as in Experimental Example 1.

The L-arginine content, L-lysine content, water content, protection rate, dissolution rate and in vitro assumed efficacy rate of the compositions of Example 9 and control A are shown in the following Table 2.

The contents of soybean fully hydrogenated oil and soybean lecithin in the molten mixture do not change before and after granulation in water.

TABLE 2

| | blending ratio [wt %] | | | | content of L-arginine in feed additive composition [wt %] | content of L-lysine in feed additive composition [wt %] | content of water in feed additive composition [wt %] | protection rate [%] | dissolution ratio [%] | in vitro assumed efficacy rate [%] |
|---|---|---|---|---|---|---|---|---|---|---|
| | (A) soybean fully hydrogenated oil | (B) soybean lecithin | (C) L-arginine | (E) L-lysine hydrochloride | | | | | | |
| control A | 49.7 | 1.3 | 49.0 | 0 | 46 | | 1.8 | 94 | 18 | 8.3 |
| Example 9 | 48.3 | 1.3 | 42.7 | 7.8 | 39 | 5.4 | 2.2 | 88 | 23.8 | 9.2 |

As is clear from the results shown in Table 2, the composition of Example 9 showed an improved dissolution rate while maintaining a high protection rate by using a small amount of L-lysine or a salt thereof (L-lysine hydrochloride) and a surfactant (lecithin) in combination as compared to the composition of control A containing a surfactant (lecithin) alone. From the results, it was confirmed that the dissolution in the intestinal tract can be further enhanced while maintaining high protection in the rumen by using a small amount of L-lysine or a salt thereof and a surfactant in combination as compared to when a surfactant alone is contained.

Experimental Example 3, Methionine

Examples 10 and 11, Control M

In the same manner as in Example 1 except that soybean fully hydrogenated oil (manufactured by Yokozeki Oil & Fat Industries Co., Ltd.), soybean lecithin (manufactured by ADM, Yelkin TS), DL-methionine (manufactured by Ajinomoto Co., Inc.), and L-lysine hydrochloride (manufactured by Ajinomoto Co., Inc.) were cast in the proportions shown in the following Table 3, the feed additive compositions for ruminants of Examples 10 and 11 and control M (hereinafter to be referred to as composition of Examples 10 and 11 and control M) were obtained.

The DL-methionine content, L-lysine content, water content, protection rate, dissolution rate and in vitro assumed efficacy rate of the compositions of Examples 10 and 11 and control M were measured and calculated in the same manner as in Experimental Example 1.

The DL-methionine content, L-lysine content, water content, protection rate, dissolution rate and in vitro assumed efficacy rate of the compositions of Examples 10 and 11 and control M are shown in the following Table 3.

The contents of soybean fully hydrogenated oil and soybean lecithin in the molten mixture do not change before and after granulation in water.

rumen by using a small amount of L-lysine or a salt thereof and a surfactant in combination as compared to when a surfactant alone is contained.

INDUSTRIAL APPLICABILITY

According to the present invention, a feed additive composition for ruminants that is provided with high protection in the rumen and is superior in dissolution in the intestinal tract can be provided.

The feed additive composition for ruminants of the present invention can further enhance dissolution in the intestinal tract while maintaining high protection in the rumen by using a small amount of L-lysine or a salt thereof in combination with a surfactant as compared to when a surfactant alone is contained.

The feed additive composition for ruminants of the present invention can further enhance dissolution in the intestinal tract while maintaining high protection in the rumen by using a particular amount of a natural vegetable oil in combination with L-lysine or a salt thereof and a surfactant.

According to the feed additive composition for ruminants of the present invention, a large amount of a biologically active substance (e.g., amino acid, etc.) can be efficiently transported up to the small intestine of a lactating cow. Therefore, the lactating cow can absorb a large amount of the biologically active substance (e.g., amino acid, etc.) as a nutrient, as a result of which, for example, it is possible to increase milk yield production and the like.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope

TABLE 3

| | blending ratio [wt %] | | | | | content of | | | | | |
|---|---|---|---|---|---|---|---|---|---|---|---|
| | (A) soybean fully hydrogenated oil | (B) soybean lecithin | (C) DL-methionine | (D) L-lysine hydrochloride | (E) olive oil | DL-methionine in feed additive composition [wt %] | content of lysine in feed additive composition [wt %] | content of water in feed additive composition [wt %] | protection rate [%] | dissolution ratio [%] | in vitro assumed efficacy rate [%] |
| control M | 41.7 | 1.3 | 57.0 | — | — | 55.0 | — | 0.1 | 97 | 3 | 1.9 |
| Example 10 | 41.7 | 1.3 | 50.8 | 6.2 | — | 48.4 | 4.6 | 0.2 | 98 | 8 | 3.7 |
| Example 11 | 41.5 | 1.3 | 50.8 | 6.2 | 0.2 | 48.2 | 4.6 | 0.2 | 98 | 11 | 5.1 |

As is clear from the results shown in Table 3, the compositions of Examples 10 and 11 showed an improved dissolution rate while maintaining a high protection rate by using a small amount of L-lysine or a salt thereof (L-lysine hydrochloride) and a surfactant (lecithin) in combination as compared to the composition of control M containing a surfactant (lecithin) alone. From the results, it was confirmed that the dissolution in the intestinal tract can be further enhanced while maintaining high protection in the of the appended claims, the invention may be practiced otherwise than as specifically described herein.

All patents and other references mentioned above are incorporated in full herein by this reference, the same as if set forth at length.

The invention claimed is:

1. A method for producing a feed additive composition for ruminants, comprising solidifying, in water, a molten mixture of (A) at least one selected from the group consisting of a hydrogenated vegetable oil and a hydrogenated animal oil each having a melting point of higher than 50° C. and lower than 90° C.;
(B) not less than 0.01 wt % and not more than 6 wt %, based on the total weight of the composition, of an additional surfactant;
(C) not less than 16 wt % and not more than 72 wt %, based on the total weight of the composition, of histidine hydrochloride, arginine, methionine or valine; and
(D) not less than 1 wt % and not more than 40 wt %, based on the total weight of the composition, of L-lysine or a salt thereof,
to obtain a solidified molten mixture.

2. The production method according to claim 1, further comprising coating said solidified molten mixture with a coating agent after the solidifying.

3. The production method according to claim 1, wherein said molten mixture further comprises:
(E) a natural vegetable oil.

4. The production method according to claim 3, wherein said feed additive composition for ruminants comprises (E) in an amount of not less than 0.01 wt % and not more than 0.8 wt %, based on the total weight of the composition.

5. The production method according to claim 1, further comprising heating said solidified molten mixture after the solidifying.

* * * * *